US00PP33958P2

(12) United States Plant Patent
Hansen

(10) Patent No.: US PP33,958 P2
(45) Date of Patent: Feb. 15, 2022

(54) ***SEDUM* PLANT NAMED 'CORALJADE'**

(50) Latin Name: ***Sedum* hybrid**
Varietal Denomination: Coraljade

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,513

(22) Filed: Jul. 27, 2021

(51) Int. Cl.
*A01H 5/02* (2018.01)
*A01H 6/32* (2018.01)

(52) U.S. Cl.
USPC ..... Plt./479

(58) Field of Classification Search
CPC ... A01H 5/02; A01H 5/00; A01H 5/12; A01H 6/32; A01H 6/328
See application file for complete search history.

*Primary Examiner* — June Hwu

(57) ABSTRACT

A new and distinct ornamental perennial *Sedum* plant named 'Coraljade' is characterized by tight-forming upright mounds of vertical stems with dark-green glaucous foliage that resists powdery mildew and subsequent scaring. The numerous, stems are highly branched and resist lodging in summer heat and rains. Individual flowers of coral-pink effect completely cover the top of the plant. The new plant is useful for the landscape in containers, as specimens or en masse.

1 Drawing Sheet

Botanical designation: *Sedum* hybrid.
Cultivar denomination: 'Coraljade'.

STATEMENT REGARDING PRIOR DISCLOSURES UNDER 37 CFR 1.77(B)(6)

The claimed plant was first sold to Willoway Nurseries, Inc. on Jul. 31, 2020 by Walters Gardens, Inc., who obtained the plant and all information relating thereto, from the inventor. Subsequently the new plant was also sold to Prides Corner Farms and Overdevest Nurseries, LP. The first non-enabling description and photographs were on a website operated by Walters Gardens, Inc. on Dec. 1, 2020, and on May 20, 2021 in the "Walters Gardens 2021-2022 Catalog." No plants of *Sedum* 'Coraljade' have been sold in this country or anywhere in the world, nor has any disclosure of the new plant been made, more than one year prior to the filing date of this application, and such sale or disclosure within one year was either derived directly or indirectly from the inventor and would be a 35 U.S.C. 102(b) exception.

BACKGROUND OF THE INVENTION

The present invention relates to a new and distinct cultivar of *Sedum* plant, botanically known as *Sedum* and hereinafter referred to by the cultivar name 'Coraljade'.

The new *Sedum* plant is a selection of a planned breeding program conducted by the inventor, at a wholesale perennial nursery in Zeeland, Mich., USA.

The new *Sedum* plant selected from a controlled insect pollination cross in an isolation block of a proprietary, unreleased, unnamed hybrid known only by the breeder code K9-116-06 with an unidentified sibling of K9-116-06 at a wholesale perennial nursery in Zeeland, Mich. The seeds were collected on Sep. 25, 2014. *Sedum* 'Coraljade' was assigned the breeder code number 14-77-6 to keep it separated from among thousands of other seedlings of this and other crosses when it progressed through the initial trial phase in the fall of 2017. The selected single seedling clone was originally selected for it strong, healthy, dense growth, colorful foliage and flowers and intermediate traits between the two parents.

Asexual reproduction of *Sedum* 'Coraljade' by division at a wholesale perennial nursery in Zeeland, Mich., USA since October of 2016, and subsequent vegetative shoot tip cuttings has shown that the unique features of this new *Sedum* plant are stable and reproduced true to type in successive generations.

SUMMARY OF THE INVENTION

Plants of *Sedum* 'Coraljade' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of *Sedum* 'Coraljade' and distinguish it as a new and distinct autumn stonecrop plant unique from all other autumn stonecrop plants known to the inventor:

1. Tight-forming upright mounds with vertical stems;
2. Center stems remain erect throughout the growing season producing full habit;
3. Glaucous, dark green foliage resists powdery mildew and the subsequent scaring;
4. Numerous stems produce dense flower clusters with coral-pink effect completely cover the top of the plant;
5. Flower buds are light green opening to pale cream with rosy pink center ovaries;

In comparison to the female parent, the new plant has a larger width and height and more basal branching and retains its upright stems better through the entire growing season. The male parent is unknown plant in the sibling block of K9-116-06.

The nearest comparison varieties known to the inventor are: 'Autumn Joy' (not patented), 'Xenox' U.S. Plant Pat. No. 16,888, 'Neon' (not patented), 'Black Jack' U.S. Plant Pat. No. 16,736, 'Lemonjade' U.S. Plant Pat. No. 26,448, 'Autumn Fire' (not patented) and 'Tiramisu' copending U.S. Plant patent application Ser. No. 17/300,509.

'Autumn Joy' is slightly taller and narrower in habit with a tendency to open more in the center, and the leaves are light grayish-green with flowers of deep rose. 'Neon' is taller and more narrow in habit, the leaves are lighter gray-green, and the flowers are a rosy-magenta that are held in more horizontal branched inflorescences. 'Black Jack' has foliage that is more greyed-purple and the flowers are deep garnet. 'Xenox' has foliage that is darker mahogany-colored, the flowers are deeper red, and the habit is more open with stems tending to lodge. 'Lemonjade' has lighter gray-green foliage and stems with citron-yellow flowers. 'Autumn Fire' has less basal branching and the inflorescences are broader and branches of the inflorescence are more horizontal and the foliage is lighter grayish-green. 'Tiramisu' has smaller leaves that are more bronze-colored, and the flowers open cream from pink blushed buds on smaller inflorescences with thinner stems and less dense flowering.

The female parent was not as stocky and full in habit, less basal branching and tended to lodge later in the season. The male parent was not as stocky and full in habit, less basal branching and tended to lodge later in the season.

BRIEF DESCRIPTION OF THE PHOTOGRAPHS

The photograph of the new plant demonstrates the unique traits and the overall appearance of *Sedum* 'Coraljade'. The colors are as accurate as reasonably possible with color reproductions of this type. Variations in ambient light spectrum, source and direction may cause the appearance of minor variation in color. The plants used in the photograph were three-year-old plants grown in an open, full-sun trial garden at a wholesale perennial nursery in Zeeland, Mich. with supplemental water and fertilizer when needed. No plant growth regulators or pinching have been used.

DETAILED BOTANICAL DESCRIPTION

Figure 1:
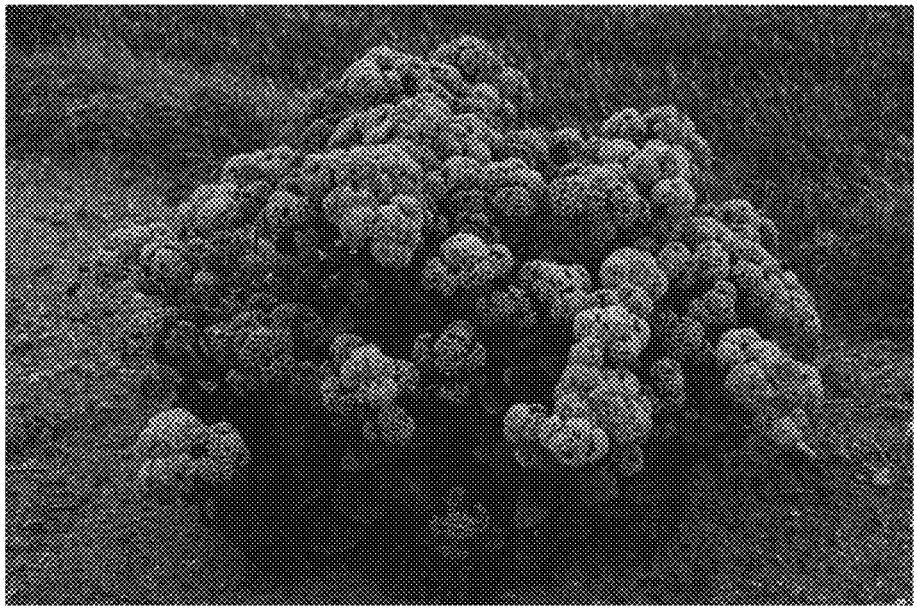
FIG. 1 shows the habit of the new plant with foliage in early stages of flowering.
Figure 2:
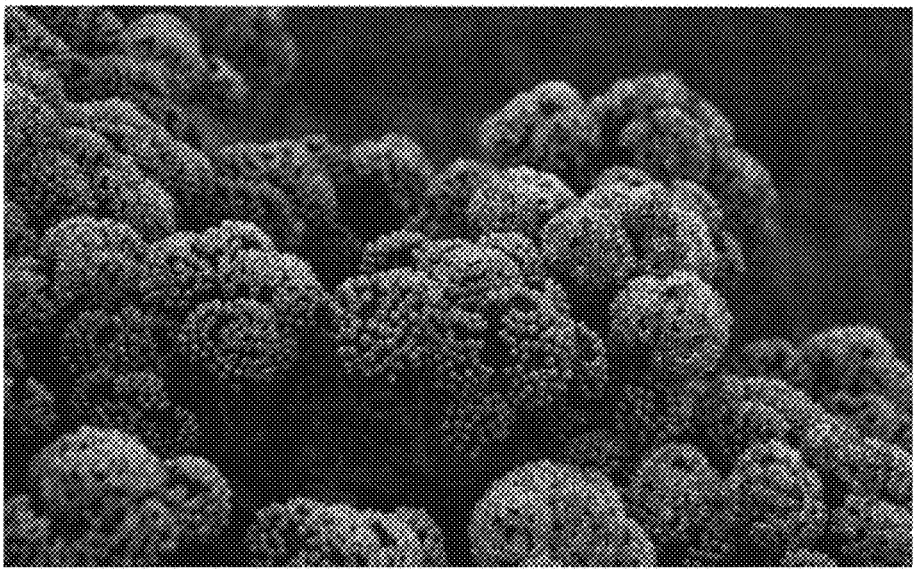
FIG. 2 shows a close-up of the flowers and buds of the new plant in mid-summer.

The following is a detailed description of three-year-old plants of the new cultivar as grown outdoors in a full sun trial plot at a wholesale nursery in Zeeland, Mich. No plant growth regulators have been used. Plants of the new cultivar have not been tested under all possible conditions. The phenotype may vary with changes in environment, climate, and cultural conditions without change however in the genotype. The color reference is in accordance with the 2015 edition of The Royal Horticultural Society Colour Chart except where general color dictionary terms are used.

Parentage: An insect pollination selection of the unreleased, unnamed proprietary hybrid known only by the breeder code K9-116-06 as the female parent and the male was an unidentified sibling of K9-116-06;

Asexual propagation: Stem tip cuttings and division;

Time to initiate roots: About two weeks;

Time to finish a 3.8 liter flowering container: About three months in the summer from a rooted 2.5 cm plug;

Root description: thick, fleshy; freely branching; creamy white to light tan in color;

Plant habit: Winter-hardy herbaceous perennial; upright mound; stiff upright stems; dense and full, not opening in center later in the season; flower heads freely branching;

Growth rate: Moderately vigorous;

Plant size: About 35.0 cm tall and 65.0 cm wide in full flower;

Stems: Terete; glaucous; glabrous; diameter at base to about 7.0 mm, average about 6.0 mm; heavily branched in distal portion; about 17.0 cm long from base to initial branches; about 15 stems per plant and 15 branches per stem;

Stem color: Variable; between a blend of RHS 145A and RHS 146D in low light and nearest RHS 147C with faint to moderate blush of nearest RHS N186C in high light; nodes variable between RHS 187D and RHS N186C;

Lateral branches: To about 15 per stem; glaucous; glabrous; terete; primary branches to about 12.0 cm long and about 4.0 mm diameter at base;

Lateral branch color: Between RHS 160D and RHS 146D in low light with heavy maculate to blush nearest RHS 187C in high light;

Foliage: Ovate to obovate; spirally arranged; flat; simple; smooth; sarcous; glabrous and glaucous on both surfaces; sessile; thick; apex bluntly acute to rounded; base shallowly cordate; margin irregularly and shallowly dentate, 15 to 18 teeth per leaf side; teeth average about 3.0 mm apart; attitude outward; about 18 leaves per stem;

Foliage size: To about 5.7 cm long, 3.5 cm across and 3.0 mm thick; average about 4.2 cm long, 2.5 cm across and 2.5 mm thick; decreasing distally;

Foliage color: Adaxial young nearest RHS 189A lightly maculate with nearest RHS N186C, abaxial young nearest RHS 189A lightly maculate with nearest RHS N186C; mature adaxial between RHS 139A and RHS 189A faintly maculate with nearest RHS N186C, mature abaxial between RHS 191A and RHS N138C; mature margins or leaf edges with moderate to strong blush nearest RHS 187B;

Petiole: Leaves sessile;

Venation: Palmate, barely distinguishable; slightly raised abaxial;

Vein color: Adaxial proximal midrib between RHS 146D and RHS 147D with moderate maculate of nearest RHS 187A, abaxial midrib between RHS 146C and RHS 147C; secondary veins both adaxial and abaxial not obvious;

Flower: Stellate; actinomophic; pentamerous; persistent; attitude upright to outwardly in terminal compound cymes; size about 5.0 mm across and 4.0 mm deep;

Flower number: To about 100 to 200 per branch and 800 to 1,200 flowers per stem and 8,000 to 18,000 per plant;

Fragrance: None detected;

Flowering season: Beginning mid-summer in Zeeland, Mich. for about three weeks;

Longevity: Flower cymes remain effective for about three weeks on the plant and one week as cut flowers; individual flowers and calyces persistent and effective for about three weeks;

Flower buds about one day prior to opening: Ellipsoidal; apex acute; base truncate; about 3.5 mm long and about 2.0 mm diameter near middle;

Flower bud color: Nearest RHS 193A; calyx nearest RHS N138D;

Inflorescence: To about 8.0 cm tall from first branch and about 14.0 cm across;

Petals: Typically five; broadly-lanceolate; acute apex; base truncate and fused; margin entire; glabrous abaxial and adaxial; average about 2.8 mm long and about 1.5 mm across at fusion;

Petal color: Young adaxial nearest RHS 145C; young abaxial between RHS 145C and RHS 193C; adaxial maturing to nearest RHS NN155B; abaxial maturing to nearest NN155A;

Calyx: With five sepals; campanulate to stellate; about 3.0 mm across and 2.0 mm deep;

Sepals: Linear to lanceolate; narrowly acute apex; fused base; entire margin; glabrous and slightly glaucous both abaxial and adaxial; adpressed to petals, about 2.0 mm long and about 0.7 mm across;

Sepal color: Abaxial and adaxial nearest RHS 138A with abaxial lightly blushed with N187C;

Peduncles: Terete; glaucous, glabrous; stiff and flexible; freely branching; mostly upwardly to slightly outwardly; with branches to about 45° from perpendicular; about 12.0 cm long and 4.0 mm diameter;

Peduncle color: Between RHS 160D and RHS 146D in low light with heavy maculate to blush nearest RHS 187C in high light;

Pedicels: Cylindrical; glabrous; glaucous; strong and stiff, yet flexible; to about 3.0 mm long and 0.7 mm diameter; average about 2.5 mm long and 0.7 mm diameter;

Pedicel color: Blend between RHS 147C and RHS 191B;

Androecium: Not observed;

Gynoecium: Typically five; cylindrical, conic in distal one third; about 3.5 mm long and 1.2 mm diameter;

*Style*.—Terete; tapering distally and base truncate; about 0.5 mm long and 0.2 mm diameter at point of attachment to ovary; glabrous; lustrous; color nearest RHS 186B.

*Stigma*.—Minute, acute; about 0.2 mm diameter and 0.1 mm long; color nearest RHS 186C.

*Ovary*.—Nearly terete, acutely tapering at apex to style; base truncate; lustrous; about 2.5 mm long and 1.2 mm diameter; color nearest RHS N155B, developing with maturity to distally nearest RHS 186B.

Fruit and seed have not been observed.

Growing conditions: Plants of the new *Sedum* 'Coraljade' is xeromorphic and grow best with good drainage, full sun and moderate to low fertility. The new plant is cold hardy from USDA zones 3 to 9 and has tolerated temperatures of at least 35 degrees C. 'Coraljade' tolerates heavy rains and wind and is not prone to develop an open center later in the season as many other *Sedum* cultivars do that are known to the inventor.

Disease and pest resistance: Other pest and disease resistance and tolerance outside that normal for *Sedum* is not known.

It is claimed:

1. A new and distinct perennial *Sedum* plant named 'Coraljade' as herein described and illustrated.

* * * * *